United States Patent [19]

Monte et al.

[11] 4,096,110

[45] Jun. 20, 1978

[54] FILLED POLYESTERS CONTAINING ORGANIC TITANATE ESTERS

[75] Inventors: Salvatore J. Monte, Staten Island, N.Y.; Gerald Sugerman, Allendale, N.J.

[73] Assignee: Kenrich Petrochemicals, Inc., Bayonne, N.J.

[21] Appl. No.: 618,223

[22] Filed: Sep. 30, 1975

Related U.S. Application Data

[63] Continuation-in-part of Ser. No. 577,922, May 15, 1975.

[51] Int. Cl.$^2$ .................................................. C08K 9/04
[52] U.S. Cl. .................................... 260/40 R; 106/299; 106/308 Q; 428/403; 428/406
[58] Field of Search ............ 428/403, 406; 260/40 R, 260/42.14; 106/299, 308 Q

[56] References Cited

U.S. PATENT DOCUMENTS

| | | | |
|---|---|---|---|
| 3,337,391 | 8/1967 | Clayton et al. | 260/429.5 X |
| 3,617,333 | 11/1971 | Brown | 428/406 X |
| 3,660,134 | 5/1972 | Morris et al. | 106/308 Q |
| 3,697,474 | 10/1972 | Morris et al. | 260/40 R |
| 3,846,359 | 11/1974 | Rostaing | 260/40 R |

FOREIGN PATENT DOCUMENTS 733,224  7/1955  United Kingdom.

*Primary Examiner*—Sandra M. Person
*Attorney, Agent, or Firm*—Bert J. Lewen

[57] ABSTRACT

A composition of matter which consists of a filled polyester composition containing specific organo-titanate salts. These salts may be represented by the following formulas:

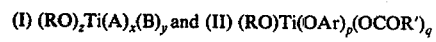

(I) $(RO)_zTi(A)_x(B)_y$ and (II) $(RO)Ti(OAr)_p(OCOR')_q$ where R is a monovalent alkyl, alkenyl, alkynyl or aralkyl group having from 1 to about 30 carbon atoms or a substituted derivative thereof; A is a monovalent sulfonic, diester pyrophosphate, diester phosphate or a substituted derivative thereof; B is OAr or OCOR'; R' is hydrogen or a monovalent organic group having 1 to about 100 carbon atoms; OAr is aryloxy; the sum of x, y and z equals 4; x and z may be 1, 2 or 3; y may be 0, 1 or 2; and p+q equals 3.

Among the advantages of the invention are improved flex modulus, flexural strength, impact strength, better mold flow and higher gloss to molded products. The physical property improvements are maintained after aging even in the presence of steam or boiling water.

12 Claims, No Drawings

FILLED POLYESTERS CONTAINING ORGANIC TITANATE ESTERS

RELATED APPLICATION

This application is a continuation-in-part of copending U.S. application Ser. No. 577,922, filed May 15, 1975.

This invention relates to new and improved filled polyester compositions containing specified organo-titanate esters. More specifically, the instant invention relates to polyester compositions having improved physical properties obtained by linking the filler to the polyester chain.

It is known that certain organic titanate esters may be used to treat the surfaces of inorganic fillers to enhance their compatibility with polymeric material. Such applications are shown in U.S. Pat. Nos. 3,660,134 and 3,697,474, issued to the Freeport Sulphur Company. These filled polymeric materials are well known and find application in fibers, sheet material and shaped solid articles. The aforesaid patents specifically relate to organic derivatives of orthotitanic acid containing at least two hydrolyzable groups.

In accordance with the instant invention, it has been found that treating inorganic fillers with selected classes of organic titanate esters imparts even greater advantages than that obtained by following the teachings of the aforesaid patents. This effect is particularly outstanding when the polymeric material is a polyester.

The first class of the organo-titanate salts which maybe used in accordance with the practice of the instant invention may be represented by the formula:

(I) $(RO)_z Ti(A)_x (B)_y$ 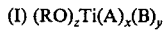

wherein R is a monovalent alkyl, alkenyl, alkynyl or aralkyl group having from 1 to about 30 carbon atoms or a substituted derivative thereof. The R group may be saturated or unsaturated, linear or branched, and may have from 1 to 6 substitutions including halogen, amino, epoxy, cyano, ether, thioether, carbonyl, aromatic, nitro or acetal. In a particular molecule, all of the R groups may be the same or different, so long as they fall within the above class. It is preferred that the R group be alkyl having 1 to 6 carbon atoms and be all the same.

The monovalent group (A) may be sulfonic, diester pyrophosphate and diester phosphate. The thioaryloxy group may be a substituted or unsubstituted thiophenoxy or thionaphthyloxy group containing up to about 60 carbon atoms. It may be substituted by alkyl, alkenyl, aryl, aralkyl, alkaryl, halo, amino, epoxy, ether, thioether, ester, cyano, carbonyl, or aromatic nitro groups. Preferably no more than three substituents per aromatic ring are present. The thioaryloxy groups wherein the aryl is phenyl or naphthyl are preferred.

The sulfonic, diester pyrophosphate and diester phosphate ligand, respectively, are represented by the following formulas:

$-OSO_2R''$, $(R''O)_2P(O)OP(OH)(O)-$ and 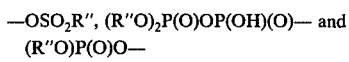
$(R''O)P(O)O-$ wherein R" may be the same as R' as defined below. Where A is a sulfonic group, it is preferred that R" be phenyl, a substituted phenyl or an aralkyl group having from 5 to 24 carbon atoms in the alkyl chain. Where A is a phosphate group, it is preferred that the R" group have from 6 to 24 carbon atoms, and where A is a pyrophosphate group, it is preferred that the R" group be alkyl having up to 12 carbon atoms.

The monovalent group (B) may be acyl (OCOR') or aryloxy (OAr). R' may be hydrogen or a monovalent organic group having from 1 to about 100 carbon atoms; particularly, an alkyl, alkenyl, aryl, aralkyl or alkaryl group. The aryl in R' and (OAr) groups may be substituted or unsubstituted phenyl or naphthyl groups, preferably containing up to 60 carbon atoms. Additionally, the R' group may be substituted with halo, amino, epoxy, ether, thioether, ester, cyano, carboxyl and/or aromatic nitro substituents. Generally up to about six substituents may occur per R' group. The R' group may contain intermediate hetero atoms such as sulfur or nitrogen in the main or pendant substituents. R' is preferably a long chain group having 18 carbon atoms. Most desirably, all R's are the same. In formula (I) the sum of x, y and z must be 4; x and z may be 1, 2 or 3; and y may be 0, 1 or 2. Preferred are those compounds where z is 1.

The second class of organic titanate salts which may be used in the practice of the present invention may be represented by the following formula:

(II) $(RO)Ti(OAr)_p (OCOR')_q$ 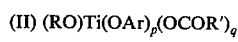

where R, R' and (OAr) are as defined above and $p+q = 3$.

Of the above classes of compounds, preferred are those where R' contains functional groups, that is, olefinic or acetylenic unsaturation, or amino or hydroxyl groups. Most preferred are such compounds wherein the R' group is polyfunctional. From the standpoint of efficiency, it is most desirable that such functional compounds have less than 8 carbon atoms. Where desired, one of the R' groups may have a long chain group in order to lower the viscosity of the filled polyester.

The aforesaid classes of organic titanate salts have distinct advantages over the ortho-titanium organic derivatives having at least two hydrolyzable groups as described in the aforesaid Freeport Sulphur Company patents. For example, with the organic titanate esters shown in Formula II, those most closely related to the aforesaid prior patents, where there is only one hydrolyzable group, the rheology of the filled polymer is improved. In the case of the phosphorus-containing compounds of Formula I, the polymeric materials are stabilized with regard to ultra-violet light and have enhanced flame retardance. The sulfur-containing compounds of Formula I show improved thermal stability and greater flex modulus as compared to the carbon compounds.

In the case of the preferred class of compounds, namely, those containing functional groups, the mechanical properties are far better than those obtained heretofore. Stress, tensile strength, flexibility, shear resistance, adhesion in surface coating applications, resistance to chemical attack and the other advantages of cross-linking are obtained. In all instances, the filler becomes more tightly incorporated in the polymeric structure. This bond results in a structure which is more readily able to transfer energy and therefore results in a stronger material.

The improved composition of the invention consists of a polyester material containing a filler which has been treated with one or more of the aforesaid organic titanate salts. Where the titanate is non-functional, the filler and the polyester are bound together by Vanderwahl's forces. On the other hand, where functional groups are present, the reaction product of the filler and the organic titanate salt is grafted to the polyester resin. Where multi-functionality is present, the compositions will in fact be cross-linked.

A broad range of polyester resins may be used in the composition and processes of this invention. In preparing the polyester, a mixture of one or more glycols and one or more alpha,beta ethylenically unsaturated polycarboxylic acids may be employed.

By way of non-limiting example, it may be mentioned that polyesters can be prepared from such acids as maleic, fumaric, aconitic, mesaconic, citraconic, ethylmaleic, pyrocinchoninic, veronic, or itaconic acid (with or without other acids) and such glycols as ethylene, diethylene, triethylene, polyethylene, 1,3-propylene, 1,2-propylene, dipropylene (1,3 or 1,2), butylene or styrene glycol.

The copolymerizable ethylenically unsaturated monomers suitable for mixing with the foregoing unsaturated polyesters are also well known and are described in full detail in the patents previously referred to. Canadian Pat. No. 703,001, issued Feb. 2, 1965, contains a particularly extensive disclosure of such monomers, and such disclosure is therefore incorporated herein by reference as showing representative monomers, any and all of which may be mixed with the polyester for use in this invention.

The preparation of the polyester itself involves heating, usually at a temperature of 280° to 480° F. for a period of from 4 to 24 hours, a mixture of one or more glycols and one or more alpha,beta-ethylenically unsaturated polycarboxylic acids. Usually a dicarboxylic acid (or its corresponding anhydride) is used. For purposes of the invention, the resulting self-condensation esterification product has, as indicated, an acid number of from 10 to 100. Such a polyester is sometimes called an "alkyd" and although it is commonly referred to as "resinous," it may be either a viscous liquid or a solid in the uncured state. In conventional practice polyesters are mixed with copolymerizable ethylenically unsaturated monomers (e.g., styrene, vinyl toluene, methyl methacrylate, vinyl acetate, diallyl phthalate, triallyl cyanurate), frequently in amounts of from 5% to 80% by weight of the mixture of polyester and monomer, and then cured to a solid, insoluble, infusible, crosslinked state with the aid of conventional catalyst systems.

The composition is characterized by the ability to be cured to a solid, infusible, insoluble, cross-linked state, under the influence of the polymerization catalyst and/or "promoters" usually used for this purpose, notably peroxidic materials, such as benzoyl peroxide, hydroperoxides such as tertiary butyl hydroperoxide, ketone peroxides such as methyl ethyl ketone peroxide, with or without such catalytic materials as cobalt, manganese and the like, as well as such promoters as N-methylaniline or the like (U.S. Pat. No. 2,449,299, Hurdis, Sept. 14, 1948), diethyl aniline or the like (Hurdis, U.S. Pat. No. 2,480,928, Sept. 6, 1949), or various other conventional catalyst mixtures. The catalyst may be used in conventional amounts, usually from 0.2 to 3% by weight of the polyester-copolymerizable monomer mixture, although larger amounts such as 4 or 5% can also be used. Cobalt or the like is usually used in the form of sufficient soluble cobalt salt (e.g., cobalt acetate, octoate, oxide or hydroxide, chloride or nitrate) to supply for example from 0.001 to 0.2%, or more of cobalt ion. The promoters are frequently used in amounts of from 0.001 to 1%, or up to 2% or more, by weight, based on the weight of polyester plus copolymerizable monomer. Depending upon the amount and kind of catalyst and promoting materials, the composition can be cured readily at essentially room temperature (e.g., frequently 60° F. to 80° F.), or, if desired, at elevated temperatures (of the order of, e.g., 120° to 350° F. for a period of from 5 minutes to 4 hours or more) particularly during the final stages of the cure.

A wide variety of ligands, subject to the limitations heretofore expressed, may be used in the practice of this invention. The most suitable depends upon the filler-polyester system and to a lesser degree upon the curative and/or extender systems employed.

Examples of specific R ligands are: methyl, propyl, cyclopropyl, cyclohexyl, tetraethyloctadecyl, 2,4-dichlorobenzyl, 1-(3-bromo-4-nitro-7-acetylnaphthyl)-ethyl, 2-cyano-furyl, 3-thiomethyl-2-ethoxy-1-propyl and methallyl.

Examples of A ligands useful in the practice of this invention include 11-thiopropyl-12-phenyloctadecylsulfonic, di(2-omega-chlorooctyl)phenyl phosphato, diisonicotinyl pyrophosphato, 2-nitro-3-iodosulfonic, 2-methallylphenoxy, phenylsulfinyl, 4-amino-2-bromo-7-naphthysulfonic, diphenyl pyrophosphato, diethylhexyl pyrophosphato, di-sec-hexylphenyl phosphato, dilauryl phosphato, methylsulfonic and laurylsulfonic. Examples of aroxy groups are 2,4-dinitro-6-octyl-7-(2-bromo-3-ethoxyphenyl)-1-naphthoyl and 3-cyano-4-methoxy-6-benzoylphenoxy.

Examples of the R' groups are numerous. These include straight chain, branched chain and cyclic alkyl groups such as hexyl, heptyl, octyl, decyl, dodecyl, tetradecyl, pentadecyl, hexadecyl, octadecyl, nonadecyl, eicosyl, docosyl, tetracosyl, cyclohexyl, cycloheptyl, and cyclooctyl. Alkenyl groups include hexenyl, octenyl and dodecenyl.

Halo-substituted groups include bromohexyl, chlorooctadecyl, iodotetradecyl and chlorooctahexenyl. One or more halogen atoms may be present, as for example in difluorohexyl or tetrabromooctyl. Ester-substituted aryl and alkyl groups include 4-carboxyethylcapryl and 3-carboxymethyltoluyl. Amino-substituted groups include aminocaproyl, aminostearyl, aminohexyl, aminolauryl and diaminooctyl.

In addition to the foregoing aliphatic groups, groups containing hetero-atoms, such as oxygen, sulfur or nitrogen, in the chain may also be used. Examples of these radicals are ethers of the alkoxyalkyl type, including methoxyhexyl and ethoxydecyl. Alkylthioalkyl groups include methylthiododecyl groups. Primary, secondary and tertiary amines may also serve as the terminal portion of the hydrophobic group. These include diisopropylamino, methylaminohexyl, and aminodecyl.

The aryl groups include the phenyl and naphthyl groups and substituted derivatives. Substituted alkyl derivatives include toluyl, xylyl, pseudocumyl, mesityl, isodurenyl, durenyl, pentamethylphenyl, ethylphenyl, n-propylphenyl, cumyl, 1,3,5-triethylphenyl, styryl, allylphenyl, diphenylmethyl, triphenylmethyl, tetraphenylmethyl, 1,3,5-triphenylphenyl. Nitro- and halo-substituted may be exemplified by chloronitrophenyl, chlorodinitrophenyl, dinitrotoluol, and trinitroxylyl.

Amine-substituted components include methylaminotoluyl, trimethylaminophenyl, diethylaminophenyl, aminomethylphenyl, diaminophenyl, ethoxyaminophenyl, chloroaminophenyl, bromoaminophenyl and phenylaminophenyl. Halo-substituted aryl groups include fluoro-, chloro-, bromo-, iodophenyl, chlorotoluyl, bromotoluyl, methoxybromophenyl, dimethylaminobromophenyl, trichlorophenyl, bromochlorophenyl, and bromoiodophenyl.

Groups derived from aromatic carboxylic acids are also useful. These include methylcarboxylphenyl, dimethylaminocarboxyltoluyl, laurylcarboxyltoluyl, nitrocarboxyltoluyl, and aminocarboxylphenyl. Groups derived from substituted alkyl esters and amides of benzoic acid may also be used. These include aminocarboxylphenyl and methoxycarboxyphenyl.

Titanates wherein R' is an epoxy group include tall oil epoxides (a mixture of 6 to 22 carbon alkyl groups) containing an average of one epoxy group per molecule and glycidol ethers of lauryl or stearyl alcohol.

Substituted naphthyl groups include nitronaphthyl, chloronaphthyl, aminonaphthyl and carboxynaphthyl groups.

Illustrative of the compounds useful in the instant invention are:

$(i-C_3H_7O)Ti(OSO_2C_6H_4C_{12}H_{25})_2(OSO_2C_6H_4NH_2)$;
$(i-C_3H_7O)Ti-[OP(O)(OC_8H_{17})_2]_3$; $(i-C_3H_7O)-Ti(OC_6H_4C(CH_3)_2C_6H_5)_3$;
$(i-C_3H_7O)Ti[OP(O)(OC_{12}H_{25})]_3$; $(i-C_3H_7O)-Ti(OCOC_{70}H_{141})_3$; $(C_6H_{12}O)Ti(OC_6H_4NH_2)_3$; $(nC_4H_9O)_2Ti[OPO(OC_6H_4C_8H_{17})_2]_2$;
$[CH_3O(CH_2)_2O]Ti(OCOC_6H_4Cl)[OP(O)(OH)OP(O)(OCH_3)_2]_2$;
$(i-C_3H_7O)(nC_{12}H_{25}O)Ti(OSO_2C_6H_5)_2$;
$(C_6H_5CH_2O)Ti(OCOC_{70}H_{141})_3$; $(i-C_3H_7O)Ti[OCOCH_2N(C_2-H_4(OC_2H_4)_{12}OCH_2C_6H_4NO_2]_3$;
$(CH_3O)Ti(OCOC_{72}H_{141})_2(OCOCH=CH_2)$;
$(Cl(CH_2)_4O)Ti[OCOC(C_{22}H_{43})_3]_2(OCOCHOC_2H_5)$;
$(nC_{16}H_{31}O)Ti[OCOC_6H_4CH_2OCH_2C_6H_3(C_{36}H_{73})_2]_2\cdot(OCOC_{70}H_{141})$;
$(i-C_3H_7O)Ti[OCOC(CH_3)=CH_2]_3$; $(i-C_3H_7O)-Ti(OCOCH_2NH_2)_3$;
$(C_6H_{11}O)Ti(OCOCH_2OCH_3)_2(OCOCHClCH_3)$; $(CH_3O)Ti(OCOCCl_3)_3$;
$(C_2H_5O)Ti(OCOCHBrCH_2Cl)(OCOC_6H_5-)(OCOCH_2NH_2)$;
$(i-C_3H_7O)Ti(OCOC_2H_5)(OCOCH_2CN)-[OCOCH_2N(CH_3)_2]$;
$(CH_3)_2CHOTi[OCO(CH_2)_{14}CH(CH_3)_2]-_2OCOC(CH_3)=CH_2$;
$(CH_3)_2CHOTi[OCO(CH_2)_{14}CH(CH_3)_2]-[OCOC(CH_3)=CH_2]_2$;

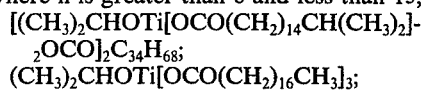

where n is greater than 8 and less than 15;
$[(CH_3)_2CHOTi[OCO(CH_2)_{14}CH(CH_3)_2]-_2OCO]_2C_{34}H_{68}$;
$(CH_3)_2CHOTi[OCO(CH_2)_{16}CH_3]_3$;

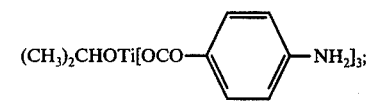

$(CH_3)_2CHOTi[OCO(CH_2)_5NH_2]_3$; $(CH_3)_2CHOTi[OCOCH_2CH_2NH_2]_3$; and

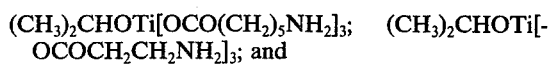

where the sum of p + q is more than 6 and less than 18.

The amount of the titanate reacted is at least 0.01 part, preferably from 0.1 to 5 parts, and most preferably between 0.2 and 2 parts, per 100 parts of inorganic solid. The optimum proportions required are a function of the inorganic solid and the alkoxy titanium salt selected, and the degree of the comminution, i.e., the effective surface area, of the inorganic solid. The reaction of the titanate takes place on the surface of the inorganic filler. The RO group splits off and an organic hydrophobic surface layer is formed on the inorganic solid. The unmodified inorganic solid is difficult to disperse in an organic medium because of its hydrophilic surface. The organo-titanium compound may be incorporated into an organic medium (low molecular weight liquids or higher molecular weight polymeric solids) with the inorganic solid. Alternatively, the organo-titanate may be first reacted with the inorganic solid in the absence of an organic medium and thereafter admixed with the latter.

By means of the present invention, the dispersion of inorganic materials in polyester polymers is improved and achieves (1) improved rheology or higher loading of the dispersate in the organic medium; (2) higher degrees of reinforcement by the use of fillers, thereby resulting in improved physical properties in the filled polymer; (3) more complete utilization of chemical reactivity, thereby reducing the quantity of inorganic reactive solids required; (4) more efficient use of pigments and opacifiers; (5) higher inorganic-to-organic ratios in a dispersion; and (6) shorter mixing times to achieve dispersion.

Also, according to the invention herein, the reaction with the RO groups on the organo-titanates may be carried out neat or in an organic medium to form a liquid, solid or paste-like solid dispersion which can be used in the compounding of the final polymeric system. Such dispersions are very stable, i.e., having little tendency to settle, separate, or harden on storage to a non-dispersible state.

The present invention results in the formation of reinforced polyesters which have a lower melt viscosity, improved physical properties, and better pigmenting characteristics than the prior art materials.

The inorganic materials may be particulate or fibrous and of varied shape or size, so long as the surfaces are reactive with the hydrolyzable group of the organo-titanium compound. Examples of inorganic reinforcing materials include metals, clay, carbon black, calcium carbonate, barium sulfate, silica, mica, glass and asbestos. Reactive inorganic materials include the metal oxides of zinc, magnesium, lead, and calcium and aluminum, and iron filings and turnings. Examples of inorganic pigments include titanium dioxide, iron oxides, zinc chromate, ultramarine blue. As a practical matter, the particle size of the inorganic materials should not be greater than 1 mm, preferably from 0.1 micron to 500 micron.

It is imperative that the alkoxy titanium salt be properly admixed with the inorganic material to permit the surface of the latter to react sufficiently. The optimum amount of the alkoxy titanium salt to be used is dependent on the effect to be achieved, the available surface area of and the bonded water in the inorganic material.

Rection is facilitated by admixing under the proper conditions. Optimum results depend on the properties of the alkoxy titanium salt, namely, whether it is a liquid or solid, and its decomposition and flash points. The particle size, the geometry of the particles, the specific gravity, the chemical composition, among other things, must be considered. Additionally, the treated inorganic material must be thoroughly admixed with the polymeric medium. The appropriate mixing conditions depend on the type of polymer, whether it is thermoplastic or thermosetting, its chemical structure, etc., as will be readily understood by those skilled in the art.

Where the inorganic material is pretreated with the organic titanate, it may be admixed in any convenient type of intensive mixer, such as a Henschel or Hobart mixer or a Waring blender. Even hand mixing may be employed. The optimum time and temperature are determined to obtain substantial reaction between the inorganic material and the organic titanate. Mixing is performed under conditions at which the organic titanate is in the liquid phase, at temperatures below the decomposition temperature. While it is desirable that the bulk of the hydrolyzable groups be reacted in this step, this is not essential where the materials are later admixed with a polymer, since the substantial completion of the reaction may take place in this latter mixing step.

Polymer processing, e.g., high shear mixing, is generally performed at a temperature well above the second order transition temperature of the polymer, desirably at a temperature where the polymers will have a low melt viscosity.

Temperatures for mixing the polyester resins with the treated filler are well known in the art. Casting resin types are best processed at room temperatures, but temperatures up to 100° C. may be used. Thermoplastic polyesters are generally processed from 200° to 325° C. A variety of mixing equipment may be used, e.g., two-roll mills, Banbury mixers, double concentric screws, counter or co-rotating twin screws and ZSK type of Werner and Pfaulder and Busse mixers.

When the organic titanate and the inorganic materials are dry-blended, thorough mixing and/or reaction is not readily achieved and the reaction may be substantially completed when the treated filler is admixed with the polymer. In this latter step, the organic titanate may also react with the polymeric material if one or more of the R' groups is reactive with the polymer.

The amount of filler used depends on the particular polymeric material, the filler and the property requirements of the finished products. Broadly, from 10 to 500 parts of filler may be used based on 100 parts of polymer, preferably from 20 to 250. The optimum amount may be readily determined by one skilled in the art.

To illustrate further the invention, attention is directed to the following examples. In certain of these examples, the number of ligands per molecule is expressed by a mixed number. In such cases, it should be understood that the structural formula represents a blend of compounds and the mixed number is the average number of such ligands in the blend.

The organic titanate esters of the invention may be readily prepared by reacting the tetraalkyl titanate with the appropriate organic acid. Examples of such preparation are set forth in copending applications, Ser. No. 556,879 filed Mar. 3, 1975 and Ser. No. 577,922 filed May 15, 1975. Examples of their preparation follow.

EXAMPLE A: PREPARATION OF ORGANO-TITANATE ESTERS

One mole of tetraisopropyl titanate is admitted to a vessel equipped with an agitator, an internal heating and cooling means, a vapor condenser, a distillate trap and liquid-solid feed input means. Agitation is commenced with the tetraisopropyl titanate at room temperature. Liquid isostearic acid is metered into the vessel at a controlled rate so that the exothermic reaction is maintained below about 350° F. until 3.19 moles of the acid are added. The isopropanol is removed from the reaction product by distillation at 150° C. at 50 mm Hg to remove potentially objectionable volatiles.

The organic titanate thus produced has an average of 3.19 moles of isostearate per molecule. The ester structure is determined by ascertaining the isopropanol liberated from the reaction and the residual isostearic acid. It is found that about from 3.1 to 3.3 moles of isopropanol are recovered in the typical run. Substantially no unreacted isostearic acid is detected. The physical properties of the ester are:

| | |
|---|---|
| Specific Gravity at 74° F. | 0.944 |
| Flash Point (COC), ° F. | 3.5 |
| Viscosity, LV, at 74° F., cps | 120 |
| Pour Point, ° F. | Below −5 |
| Decomposition Point, ° F. | Above 400 |
| Gardner Color | 15 Max |
| Appearance | Reddish Oily Liquid |

EXAMPLE B: PREPARATION OF $(i\text{-}C_3H_7O)_{0.7}Ti(OCOC(CH_3)=CH_2)_{3.3}$ One mole of tetraisopropyl titanate is added to a vessel such as described in Example A, and stirring commenced. Liquid methacrylic acid is added at a controlled rate so that the exothermic reaction is maintained below about 180° C. until 3.50 moles of the acid are added. Isopropanol is removed from the reaction product by distillation at 150° C. at 50 mm Hg to remove volatiles.

The organic titanate thus produced has an average of 3.3 moles of methacrylate per molecule. The product structure is determined by ascertaining the isopropanol liberated from the reaction and the residual methacrylic acid. From 3.1 to 3.3 moles of isopropanol are recovered. About 0.2 mole methacrylic acid plus isopropyl methacrylate are detected. The physical properties of the product are:

| | |
|---|---|
| Specific Gravity at 24° C. | 0.92 |
| Flash Point (COC), ° C | 120 |
| Pour Point, ° C | About 130 |
| Decomposition Point, ° C. | Above 200 |
| Appearance | Tan Solid |

The following examples illustrate the practice of the instant invention:

EXAMPLE 1

This example teaches the use of compounds of this invention, viz., (A) $(CH_3O)Ti(OCOCH=CH_2)_3$, (B) $(i\text{-}C_3H_7O)Ti[OCOC(CH_3)=CH_2]_3$, (C) $(i\text{-}C_3H_7O)_2Ti(OSO_2CH_2CH_2COCH=CH_2)_2$ and (D)

$(BrCH_2CH_2O)Ti[(OP(O)(OCH_2CH=CH_2)]_3$ as flex property modifiers for polyester resin.

Formulations were prepared containing 100 parts of a cobalt activated polyester resin (GR 643, a trademark of W. R. Grace Co.), 1 part of methyl ethyl ketone peroxide, 60 parts of high surface area calcium carbonate, and 0.3 part of alkoxy titanium salt, as indicated in the Table below.

Samples measuring ½ inch × 5 inches × ⅛ inch thick were cast and cured at ambient temperature for 30 minutes. The castings were tested and the results shown in Table A below:

Table A

| Alkoxy Titanium Salt | Flex Modulus psi | Flexural Strength psi |
|---|---|---|
| None | $1.5 \times 10^6$ | $4 \times 10^3$ |
| A | $3.5 \times 10^6$ | $7 \times 10^3$ |
| B | $4.0 \times 10^6$ | $10 \times 10^3$ |
| C | $2.0 \times 10^6$ | $6 \times 10^3$ |
| D | $1.0 \times 10^6$ | $8 \times 10^3$ |

The above data establish clearly the improved flexural properties obtained by the use of the organo-titanates of the invention.

EXAMPLE II

This example shows the effect of isopropyl dimethacryl isostearoyl titanate (E) and isopropyl triisostearoyl titanate (F) on the properties of a mineral-filled polyester employing a variety of fillers. The polyester employed was the same as that described in Example I. The titanate compound was premixed with the filler in a Waring blender. Thereafter, the treated filler was added to the polyester, mixed and then cured with methylethyl ketone peroxide at 22° C. Table B shows the effect of the titanate treatment on the physical properties of the cured polyester tested at ambient temperature.

Table B

| Filler | Wt. % | Alkoxy Titanate Wt. % | Flex Modulus, psi × $10^6$ | Flexural Strength psi × $10^3$ | Izod Impact ft.lb/in. Notch |
|---|---|---|---|---|---|
| Hydrated alumina (Five micron particle size) | 67 | None | 1.76 | 4.4 | 0.198 |
|  | 67 | (E) 1.35 | 1.00 | 3.7 | 0.300 |
| Calcium carbonate (One micron particle size) | 67 | None | 1.19 | 5.25 | 0.288 |
|  | 67 | (E) 1.35 | 0.42 | 3.25 | 0.392 |
| Silica (One micron particle size) | 67 | None | 3.0 | 4.7 | 0.287 |
|  | 67 | (E) 1.35 | 1.3 | 5.1 | 0.283 |
|  | 35 | None | 1.54 | 7.0 |  |
|  | 35 | (E) 0.35 | 1.81 | 7.0 |  |
|  | 35 | (F) 0.35 | 0.93 | 6.55 |  |

The above data clearly show the improvement obtained by treating the filler with the isopropyl dimethacryl isostearoyl titanate (E). Depending on the particular filler employed and the filler loading, improvement is shown in the Izod Impact Strength, the flexural strength, and the flex modulus of the cured compositions. In the case of the unsaturated titanate, namely, the isopropyl triisostearoyl titanate (F), the flex modulus was decreased. This shows the superiority of the unsaturated titanates with regard to the properties tested.

EXAMPLE III

This example shows the effect of titanate coupling agents on the viscosity of a dispersion of calcium carbonate (particle size 5 microns) in a low molecular weight polyester plasticizer (Paraplex G33, trademark of Rohm & Haas Co. for polyethylene adipate, mol. wt. ca. 1000). One part by weight of each titanate indicated below was added to separate samples containing 30 parts by weight of the plasticizer and 70 parts by weight of the filler. Mixing was done with the aid of a Waring blender. The following results were obtained:

TABLE C

| Alkoxy Titanate Salt | Dispersion Viscosity × $10^3$ at 28° C. | | | |
|---|---|---|---|---|
|  | Initial | ¼ Hr. | 1 Day | 7 Days |
| None | 11.5 | 12.3 | 13.0 | 11.5 |
| Isopropyl triisostearoyl | 28.0 | 29.0 | 29.0 | 29.5 |
| Isopropyl tri(dodecylbenzenesulfonic | 245.0 | 180.0 | 110.0 | 24.0 |
| Isopropyl tri(dioctylphosphato) | 10.5 | 15.8 | 29.2 | 40.7 |

The above data show that a full range of viscosity control can be achieved. Increased viscosity is particularly important as it improves the thixotropic properties of the dispersion. This is useful in applications such as painting and printing. The phosphate formulation's comparatively low viscosity facilitates mixing while giving high viscosity useful in later applications. Viscosity tests were also made on polyester compositions containing the following titanates. The number in parenthesis after the compound is the viscosity determined: isopropyl dimethacryl isostearoyl (18.0); isopropyl dimethacryl isostearoyl (25.5); isopropyl di(dodecylbenzenesulfonic p-aminobenzene sulfonic (21.5); and isopropyl tri(dioctylpyrophosphato) (8.7). The pyrophosphate is unique in its ability to decrease viscosity: an effect of importance in reducing energy requirements for mixing.

EXAMPLE IV

The effect of isopropyl tridodecylbenzenesulfonyl titanate on the viscosity of a calcium carbonate (5 micron particle size) dispersion in a 500 molecular weight (polyethylene glycol adipate) polyester was determined. The dispersion contains 33 wt. % of calcium carbonate. 0.5 part of the titanate was added and thoroughly mixed in the polyester. The initial Brookfield viscosity at 25° C. was 1625 centipoise for the control and 1600 centipoise after aging for 24 hours at 150° C. On the other hand, the viscosity of the treated material was initially 2900 centipoise and 4700 after aging. This increase in viscosity is advantageous because it allows the formulation to be blended at low viscosity and, upon aging, give a higher viscosity useful in many applications.

EXAMPLE V

The effect of isopropyl trimethacryl titanate (G), isopropyl tri(dioctylphosphato)titanate (H), isopropyl triacryl titanate (I) and isopropyl didodecylbenzene sulfonyl, 4-aminobenzene-sulfonyl titanate (J) on the flexural strength of 50% Wollastonite P-1 (trademark of Interpace Corporation of a naturally occurring calcium-magnesium-aluminum silicate fiber) filled polyester resin is demonstrated in this example. (The polyester was that described in Example I.) One weight percent of each titanate was premixed with the filler by dry blending in a Waring blender. The treated filler was then thoroughly blended with the polyester. The resulting dispersion was cured at room temperature. The following results were obtained:

Table D

| Alkoxy Titanium Salt | Flexural Strength, psi |
|---|---|
| None | 14,000 |
| (G) | 21,500 |
| (H) | 18,200 |
| (I) | 24,400 |
| (J) | 16,300 |

The above data show the increased flexural strength of the filler polyester treated according to the invention. The olefinically unsaturated titanates gave the best result.

EXAMPLE VI

Two unsaturated triglyceride alkyd polyester surface coatings were prepared and laminated on fiberboard substrates. The formulations and curing conditions were as follows:

| Components, pts. by wt. | Coating A | Coating B |
|---|---|---|
| Polyester | 85 | 85 |
| Melamine | 15 | 15 |
| Titanium dioxide (Rutile) | 95 | 95 |
| Toluene sulfonic acid | catalytic amount | |
| Volatile organic solvent | 40 | 20 |
| Isopropyl dioctylphosphato titanate | — | 1.1 |
| Cure time, min. | 15 | 15 |
| Cure temperature, ° C. | 191 | 135 |

The cured coatings were tested for pencil hardness. The titanate modified coating, B, had a hardness of H while the unmodified coating was substantially softer, B hardness.

After 100 hours of a 5% salt spray at room temperature, the coating of the invention had less than ⅛ inch of creepage at the scribe, while coating A had a creepage of ¼ inch. This shows superior dimensional stability. Furthermore, the reverse impact strength was qualitatively superior.

In coating B, because of improved flow, only one-half the solvent was required. This reduces the energy required to drive off solvent and to cure and the cost of the coating.

We claim:

1. A filled polyester composition comprising a polyester resin containing a filler which has been treated with an organic titanate compound having the formula: $(RO)_z Ti(A)_x(B)_y$, wherein R is a monovalent alkyl, alkenyl, alkynyl, or aralkyl group having from 1 to 30 carbon atoms or substituted derivatives thereof; A is a sulfonic, a diester pyrophosphate, a diester phosphate, or substituted derivative thereof; B is OAr or OCOR'; R' is hydrogen or a monovalent organic group having from 1 to 100 carbon atoms; OAr is aroxy; $x + y + z = 4$; x and z may be 1, 2 or 3; and y may be 0, 1 or 2.

2. The filled polyester composition of claim 1 wherein A is a sulfonyl group having the formula $OSO_2R''$; R'' is a phenyl, substituted phenyl, or an aralkyl group having from 5 to 24 carbon atoms; R is an alkyl group having from 1 to 6 carbon atoms; and z is 1.

3. The filled polyester composition of claim 2 wherein the R'' group is dodecylbenzene.

4. The filled polyester composition of claim 1 wherein the A group is a diester pyrophosphate having the formula $(R''O)_2 P(O)OP(OH)O$—; R'' is an alkyl group having up to 12 carbon atoms; R is an alkyl group having from 1 to 6 carbon atoms; and z is 1.

5. The filled polyester composition of claim 4 wherein the R'' group is octyl.

6. The filled polyester composition of claim 1 wherein the A group is a diester pyrophosphate having the formula $(R''O)_2 P(O)O$—; wherein R'' is an alkyl group having from 6 to 24 carbon atoms; R is an alkyl group having 1 to 6 carbon atoms; and z is 1.

7. The filled polyester composition of claim 6 wherein R'' is octyl.

8. The filled polyester composition of claim 1 wherein at least one of the R' groups is a long chain alkyl group.

9. A filled polyester composition comprising a polyester resin containing a filler which has been treated with an organic titanate compound having the formula: $(RO)Ti(OAr)_p(OCOR')_q$ wherein R is a monovalent alkyl group having from 1 to 6 carbon atoms or substituted derivatives thereof; R' is hydrogen or a monovalent organic group having from 1 to 100 carbon atoms, at least one of which is a monofunctional organic group having a functional olefinic acetylenic, amine or hydroxy group and less than 8 carbon atoms; OAr is aroxy; and $p + q = 3$.

10. The filled polyester composition of claim 9 wherein R is an alkyl group having 1 to 6 carbon atoms, q is 3 and R' is an acryl or methacryl group.

11. A filled polyester composition which comprises a polyester resin containing a filler which has been treated with from 0.1 to 5 weight percent of isopropyl dimethacryl isostearoyl titanate.

12. A filled polyester composition which comprises a polyester resin containing a filler which has been treated with from 0.1 to 5 weight percent of isopropyl tri(dioctylpyrophosphato)titanate.

* * * * *